United States Patent [19]

Kim et al.

[11] 4,179,403
[45] Dec. 18, 1979

[54] RESIN-LIGAND-METAL COMPLEX COMPOSITIONS

[75] Inventors: Leo Kim; Timm E. Paxson; Sunny C. Tang, all of Houston, Tex.

[73] Assignee: Shell Oil Company, Houston, Tex.

[21] Appl. No.: 861,916

[22] Filed: Dec. 19, 1977

[51] Int. Cl.$^2$ ...................... B01J 31/08; B01J 31/10
[52] U.S. Cl. ............................ 252/431 C; 585/277; 585/645; 252/431 N; 252/431 P; 260/449.6 R; 260/449 R; 560/233; 260/604 HF
[58] Field of Search ........... 252/429 R, 431 R, 431 C, 252/431 N, 431 P

[56] References Cited

U.S. PATENT DOCUMENTS

| | | | |
|---|---|---|---|
| 3,726,809 | 4/1973 | Allum et al. | 252/431 P |
| 3,847,997 | 11/1974 | Allen | 252/431 P X |
| 3,872,026 | 3/1975 | Dunn | 252/431 N X |
| 3,900,557 | 8/1975 | Strathdee | 252/431 P X |
| 3,907,852 | 9/1975 | Oswald et al. | 252/431 N X |
| 3,980,583 | 9/1976 | Mitchell et al. | 252/431 N X |
| 3,998,864 | 12/1976 | Trevillyan | 252/431 P X |
| 4,045,493 | 8/1977 | Trevillyan | 252/431 P X |
| 4,053,534 | 10/1977 | Mitchell et al. | 260/683.15 R |
| 4,072,720 | 2/1978 | Haag et al. | 252/431 N X |
| 4,098,727 | 7/1978 | Haag et al. | 252/431 R X |
| 4,111,856 | 9/1978 | Haag et al. | 252/431 N X |

OTHER PUBLICATIONS

Pittman et al., "Polymer-bound Catalysts", Chemtech, Sep. 1973, pp. 560–566.
Lapporte et al., J. Org. Chem., 28 (Jul., 1963) pp. 1947–1948.

Primary Examiner—Patrick Garvin
Attorney, Agent, or Firm—Howard W. Haworth

[57] ABSTRACT

A composition comprising an ion exchange resin and an organic linking compound having at least one resin-compatible moiety ionically bound to said resin and further having at least one metal complexible moiety selected from the group consisting of trivalent nitrogen, trivalent phosphorus, trivalent arsenic, trivalent bismuth and trivalent antimony complexed to a metal selected from Group IVB, VB, VIB, VIIB, VIII and IB metals, said composition being useful in heterogeneous catalysis.

9 Claims, No Drawings

RESIN-LIGAND-METAL COMPLEX COMPOSITIONS

BACKGROUND OF THE INVENTION

1. Field of the Invention

This invention relates to a composition comprising an ion exchange resin with a ligand ionically bounded thereto and with the ligand coordinately bonded to a transition element.

2. The Prior Art

The use of heterogeneous catalysts over homogeneous catalysts has several advantages such as allowing the use of fixed beds, ease of separation of catalyst from the product and catalyst recovery and regeneration.

Traditionally, to produce heterogeneous catalysts from metals of the transition element series, these metals have been deposited on inert supports such as alumina or silica. More recently metal catalysts have been covalently attached to inert resin backbones by use of diphenylphosphine or other ligands which are attached directly to the polymer and coordinately bonded to the metal. Typical examples of this type are found in U.S. Pat. No. 3,998,864, issued Dec. 21, 1976, and in Pittman et al. *Chemtech*, p. 560–566, 1973.

In the composition of the invention, on the other hand, the metal is coordinately bound to a ligand and the ligand is ionically bound to an ion exchange resin. Some of the advantages of the materials of the invention are that the materials are relatively simple to prepare using commercially available compounds, the preparations involve no exotic conditions, and often times may be carried out in an aqueous solvent system and the resins may be easily stripped of metal and ligands for isolation of the metal species and regeneration of the catalyst. The resin based catalysts of this invention have unique selectivity-reactivity properties when compared to their homogeneous analogues.

SUMMARY OF THE INVENTION

The invention provides a method whereby metals can be attached to ion exchange resins via an intermediate ligand. Specifically, this invention is directed to the composition produced thereby which comprises (a) an ion exchange resin, (b) a metal selected from the transition group of elements and (c) a linking compound which has at least one moiety coordinately bound to the metal and further has at least one moiety which is ionically bonded to the ion exchange resins. The compositions of this invention are particularly useful as heterogeneous catalysts.

DESCRIPTION OF THE PREFERRED EMBODIMENTS

The ion exchange resins utilized in the composition of this invention are well known in the art and are readily available commercially. These are in the gel form or are macroporous and are either strongly acidic, weakly acidic, strongly basic, intermediate basic, weakly basic or mixed acid-base. The strong acid resins typically have base resins of cross-linked styrene, styrene-divinylbenzene, phenol-formaldehyde, benzene-formaldehyde, having functional sulfonic or phosphonic acid groups attached thereto. Also suitable are the fluorinated alkyl sulfonic acid resins containing the -$CFSO_3H$ group as, for example, the NAFION ® type resins supplied by E. I. Du Pont De Nemours. The weak acid resins are those with carboxylic acid groups and are typically acrylic acid derivatives such as, for example, those resins prepared by the copolymerization of methacrylic acid and divinylbenzene. Another weak acid resin is the chelating type which is a styrene-divinylbenzene copolymer containing iminodiacetic acid functional groups which can serve as an anion exchanger at very low pH. The basic resins typically have base resins of cross-linked styrene, styrene-divinylbenzene, phenol-formaldehyde, benzene-formaldehyde, epoxypolyamine, phenolic-polyamine having functional amine, either primary, secondary, tertiary or quaternary, or pyridinium groups attached thereto. Typical examples of suitable commercially supplied resins are given in Table I (reference: Bio-Rad Laboratories Catalogue, Chromatography, Electrophases, Immunochemistry and Membrane Filtration, Price List C, March 1977, p. 11).

TABLE 1

| Type and Exchange Group | Bio-Rad | Dow Chem. Company "Dowex" | Diamond-Shamrock "Duolite" | Rohm & Haas Co. "Amberlite" | Permutit Company (England) | Permutit Company (U.S.A.) |
|---|---|---|---|---|---|---|
| Anion exchange resins | | | | | | |
| Strongly Basic, polystyrene | AG 1-X1 | 1-X1 | | | DeAcidite FF (lightly crosslinked) | S-100 |
| φ-$CH_2N^+(CH_3)_3Cl^-$ | AG 1-X2 | 1-X2 | | | | |
| | AG 1-X4 | 1-X4 | A-101D | IRA-401 | | |
| | AG 1-X8 | 1-X8 | | IRA-400 CG 400 | DeAcidite FF | |
| | AG 1-X10 | 1-X10 | | IRA-425 | | |
| φ-$CH_2N^+(CH_3)_2(C_2H_4OH)$ $Cl^-$ | AG 21K | 21K | | IRA-402 | | |
| 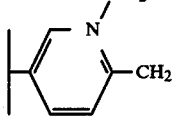 | AG 2-X4 | 2-X4 | A-102D | | | S-200 |
| | AG 2-X8 | 2-X8 | | IRA-410 | | |
| | AG 2-X10 | | | | | |
| | Bio-Rex 9 | | | | | A-580 |
| Intermediate Base, epoxypolyamine R—$N^+(CH_3)_2Cl^-$ and R—$N^+(CH_3)_2(C_2H_4OH)$ $Cl^-$ | Bio-Rex 5 | | A-30B | | F | S-310 S-380 |
| Weakly Basic, polystyrene or phenolic polyamine φ-$CH_2N^+(R)_2Cl^-$ | AG 3-X4 A | WGR | A-6 A-7 A-4F | IR-45 IR-4B IRA-68 | G | S-300 S-350 |
| Cation exchange resins | | | | | | |
| Strong Acidic, phenolic R—$CH_2SO_3H^+$ | Bio-Rex 40 | | C-3 | | Zeocarb 215 | |

TABLE 1-continued

| Type and Exchange Group | Bio-Rad | Dow Chem. Company "Dowex" | Diamond-Shamrock "Duolite" | Rohm & Haas Co. "Amberlite" | Permutit Company (England) | Permutit Company (U.S.A.) |
|---|---|---|---|---|---|---|
| Strong Acidic, polystyrene $\phi\text{-}SO_3^-H^+$ | | AG 50W-X1 | 50W-X1 | | | |
| | | AG 50W-X2 | 50W-X2 | | IR-116 | |
| | | AG-50W-X4 | 50W-X4 | | IR-118 | Zeocarb 225 (X4) |
| | | AG 50W-X8 | 50W-X8 | C-20 | IR-120 | Zeocarb 225 | Permutit Q |
| | | | | | CG-120 | | |
| | | AG 50W-X10 | 50W-X10 | C-20X10 | IR-122 | | Q-100 |
| | | AG 50W-X12 | 50W-X12 | C-20X12 | IR-124 | | Q-110 |
| | | AG 50W-X16 | 50W-X16 | | | | Q-130 |
| Weakly Acidic, acrylic $R\text{—}COO^-Na^+$ | Bio-Rex 70 | | | IRC-50 | | Q-210 |
| | | | CC-3 | CG-50 | Zeocarb 226 | |
| Weakly Acidic, chelating resin, polystyrene $\phi\text{-}CH_2N\begin{smallmatrix}CH_2COO^-H^+\\CH_2COO^-H^+\end{smallmatrix}$ | Chelex 100 | A-1 | | | | |
| Macroporous resins | | | | | | |
| Strong Base, polystyrene $\phi\text{-}CH_2N^+(CH_3)_3Cl^-$ | | AG MP-1 | MSA-1 | A-161 | IRA-900 | |
| Strong Acid, polystyrene $\phi\text{-}SO_3^-H^+$ | | AG MP-50 | MSC-1 | C-25D | 200 | |
| Mixed bed resins | | | | | | |
| $\phi\text{-}SO_3^-H^+$ & $\phi\text{-}CH_2N^+(CH_3)_2OH^-$ | | AG 501-X8 | | GPM-331 G | MB-1 | Bio-Demineralit | M-100 |

The preferred resin choice for the composition of this invention will depend on the particular ionically bondable moiety utilized on the linking compound as well as on the particular use envisioned for the composition. For example, if the composition were used in liquid-phase catalysis, the composition and pH of the liquid would determine the preferred resin to be utilized.

The linking compound is hydrocarbyl, i.e., alkyl, aryl, or mixtures of aryl and alkyl components, which can be either cyclic or acylic or mixtures thereof containing from 1 to about 100 carbon atoms, preferably from about 3 to about 80 carbon atoms and has at least two moieties containing an atom other than carbon.

At least one moiety is in the ionic or ionizable form and is compatible with the exchange group on the ion exchange resin, i.e., when the exchange group is acidic the resin-compatible ionic moiety on the linking compound is basic-derived and vice versa. The acidic-derived resin compatible ion moiety is derived from carboxylic acid ($RCO_2^-$), phosphonic acid ($RPO(OH)O^-$), phosphinic acid ($R_2POO^-$), sulfenic acid ($RSO^-$), sulfinic acid ($RSOO^-$), sulfonic acid ($RSO_2O^-$), boronic acid ($RB(OH)O^-$), boronous acid ($RBO^-$). The basic-derived resin compatible ion moiety is monohydrocarbyl ammonium ($RN^+H_3$), dihydrocarbyl ammonium ($R_2N^+H_2$), trihydrocarbyl ammonium ($R_3N^+H$), quarternary ammonium ($R_4N^+$), pyridinium ($RC_5H_4N^+R_1$), phosphonium ($R_4P^+$), arsonium ($R_4As^+$), and sulfonium ($R_3S^+$).

The linking compound may have more than one of the ionic moieties. It may be polyfunctional, for example, in carboxylate ion, in phosphonate ion, in sulfonate ion, in quaternary ammonium ion, in pyridinium and the like. The polyfunctional group may be the same or different.

At least one other moiety of the linking compound has an atom capable of complexing with metals from the transition element series, and consists of trivalent nitrogen, trivalent phosphorus, trivalent arsenic, trivalent bismuth, and trivalent antimony.

The three valences of the complexing atoms may be satisfied by any organic radical; saturated or unsaturated aliphatic, and/or saturated or unsaturated heterocyclic and/or aromatic radicals. These radicals may contain any functional group such as carbonyl, nitro, and hydroxy groups as well as saturated and unsaturated alkyl groups and the radical may be bonded to the complexing atom directly through a carbon-complexing atom linkage or through an electronegative atom such as oxygen or sulfur.

It is also suitable for a simple organic radical to satisfy more than one of the valence of the complexing atom, thereby forming a heterocyclic compound with the trivalent complexing atom. For example, an alkylene radical may satisfy two of the valences thereby forming a cyclic compound. Another example would be the alkylene dioxy radical to form a cyclic compound where oxygen atoms link an alkylene radical to the complexing atom. In these two examples the third valence may be satisfied by any other organic radical.

The linking compound may have more than one of the metal-complexing moieties. It may be, for example, polydentate in phosphorus atom, e.g., it may be bi- or tridentate, having two or three phosphorus atoms. It may have mixed complexing atoms, e.g., a phosphorus and arsenic atom or two phosphorus atoms and one nitrogen atom, etc.

The trivalent nitrogen atom will be present as an amine, i.e., as a primary, secondary, tertiary, quaternary amine or as pyridine or cyanide. The trivalent phosphorus will be present as phosphine ($R_3P$), phosphinite ($ROPR_2$), phosphonite ($RO)_2PR$ and phosphite ($RO_3P$). Correspondingly, trivalent arsenic will be available as arsine, arsinite, arsonite and arsenite; trivalent bismuth as bismuthine, bismuthinite, bismuthonite and bismuthite; and trivalent antimony as stibine, stibinite, stibonite and stibite. The preferred complexing atoms are phosphorus and nitrogen. The tertiary amines, phosphines, arsines and stibines and bismuthines have a marked tendency to form nonionic complexes with metals.

When the linking compound is polydentate in an ionizable heteroatom, it is understood that there will be a statistical distribution of the ionized atoms upon quaternization or protonation. For example, if one mole of a linking compound which contains 3 amine groups is protonated with 2 moles of HCl, then some of the molecules of the linking compound will have 3 quaternized amine groups, some will have 2 and some will have 1, but on the average there will be 2 quaternized amino group per molecule. It is further understood from general principles of organic chemistry that unit charges resulting from quaternization and protonation can be distributed as partial charges over several heteroatoms in a linking compound molecule.

Thus the linking compound as reacted in the composition of this invention will have at least one protonized or quaternized heteroatom and at least one heteroatom complexed with a transition element metal. Suitable linking compounds utilized in making the composition of the invention include but are not limited to the following examples:

tris(dimethylamino)phosphine
   tris(diethylamine)phosphine
   tris(diisopropylamino)phosphine
   tris(methylethylamino)phosphine
   tris(p-dimethylaminophenyl)phosphine
   tris(p-diethylaminophenyl)phosphine
   tris(p-methylethylaminophenyl)phosphine
   tris(o-dimethylaminophenyl)phosphine
   tris(m-dimethylaminophenyl)phosphine
   tris(dimethylaminoethyl)phosphine
   tris(dimethylaminoethyl)phosphite
   ethylbis(diphenylphosphinoethyl)amine Substitution of phosphinites, phosphonites, phosphites for the phosphine in the above compounds as well as arsines, arsinites, arsonites, arsenites, bismuthenes, bismuthinites, bismuthonites, bismuthites, stibines, stibinites, stibonites, stibites and amines produces linking compounds useful in preparing the compositions of this invention. Other suitable compounds are:

tris(4-N,N-dimethylaminophenyl)phosphine
   2-(P,P-diphenylphosphino)benzoic acid
   tris(beta-aminoethyl)amine
   2-chloronicotinic acid, and 2-carboxypyridine
   1,1-dimethyl-4-phenyl piperazinium salt
   2,2'-alkylarsino-1,1'-diphenylamine
   2-(P,P-dicyclohexylphosphino)benzoic acid
   beta-(dicyclohexylphosphino)propionic acid
   1,4-(P,P-diphenylphosphino)benzene
   2-diphenylphosphino-3-carboxy-2-butene
   2-(P,P-diphenylphosphino)benzene sulfonic acid
   2-amino-s-triazine
   1-diphenylphosphino-2-diphenylposphinoethane
   tris-(B-N,N-dimethylaminoethyl)phosphite
   tris(N,N-dimethylamino)phosphine
   bis-(B-diphenylphosphinoethyl)ethylamine
   3-(dialkylphosphino)benzene phosphonic acid The metals complexed with the linking compound are selected from the transition elements of the Periodic Table and preferably are selected from Groups IVB, VB, VIB, VIIB, VIII, IB and IIB, technetium excluded, i.e., preferred metals are:

TABLE I

| IVB | VB | VIB | VIIB | VIII | IB | IIB |
|---|---|---|---|---|---|---|
| Ti | V | Cr | Mn | Fe Co Ni | Cu | Zn |

TABLE I-continued

| IVB | VB | VIB | VIIB | VIII | IB | IIB |
|---|---|---|---|---|---|---|
| Zr | Nb | Mo | — | Ru Rh Pd | Ag | Cd |
| Hf | Ta | W | Re | Os Ir Pt | Au | Hg |

Preferred metals are from Groups VIB, VIIB, VIII and IB.

The complexed metals can be in various oxidation states. See "Complexes of the Transition Metals with Phosphines, Arsines and Stibines", by G. Booth, Adv. Inorg. Nucl. Chem., 6, 1–69 (1964) for a comprehensive description of complexes. For example, the Booth reference cites the following oxidation states for metals complexed with phosphines.

TABLE II

| Metal | Oxidation State for Stable Phosphine Complexes |
|---|---|
| Ti | 4 |
| Zr | 4 |
| Hf | 4 |
| V | 0, 3, 4 |
| Cr | 0, 2, 3 |
| Mo | 0, 1, 2, 3, 4 |
| W | 0, 1, 2, 3, 4 |
| Mn | 0, 1 |
| Re | 0, 1, 2, 3, 4, 5 |
| Fe | 0, 1, 2, 3 |
| Ru | 0, 2, 3, 4 |
| Os | 2, 3, 4 |
| Co | 1, 2, 3 |
| Rh | 0, 1, 3 |
| Ir | 1, 3 |
| Ni | 0, 1, 2, 3 |
| Pd | 0, 2 |
| Pt | 0, 2 |
| Cu | 1, 3 |
| Ag | 1 |
| Au | 1, 3. |

Articles dealing with the complexing of amines with metals are "Inorganic Complexes", Jorgensen, C. K., Academic Press 1963, chap. 4 and "Chemistry Coordination Compounds", Bailer (Ed.), Am. Chem. Soc. Monograph Series 131, 1956. The above references cite the following oxidation states for metals complexed with amines.

TABLE III

| Metal | Oxidation State of Stable Amine Complexes |
|---|---|
| Cr | 0, 1, 2, 3 |
| Mo | 0, 3 |
| W | 2 and 3 (polynuclear), 4 (mononuclear) |
| Mn | 2 |
| Re | 3, 5 |
| Fe | 2, 3 |
| Ru | 2, 3 |
| Os | 2, 3, 4 |
| Co | 2, 3 |
| Rh | 3 |
| Ir | 3, 4 |
| Ni | 0, 2 |
| Pd | 2 |
| Pt | 0, 2, 4 |
| Cu | 2 |
| Ag | 1, 2 |
| Au | 3 |

The composition of the invention may have more than one transition element metal present. The composition may also have the metal(s) co-complexed with other ligands in addition to the linking compound. For example, from the above-noted Booth reference the metal complexed moiety of the composition could have the following form and still be within the scope of the invention, i.e.,

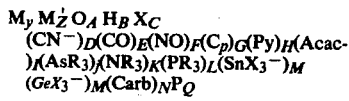

$M_y$ = metal in oxidation state shown in Table II or Table III
  Y = 0 to n mononuclear to polynuclear cluster
$M_z$ = metal in oxidation state shown in page 1
  Z = 0 to n mononuclear or mixed metal polynuclear cluster where n is an integer greater than 0 when Y>0 and Z>0
O = oxygen where
  A = 0 to n
H = hydrogen where
  B = 0 to n
X = halide F, Cl, Br, I; where
  C = 0 to 5
$(CN^-)$ = cyanide where
  D = 0 to 5 when y+z=1 or D=1 to n when y+z>1
(CO) = carbonyl where
  E = 0 to 5 when y+z=1 or E=1 to n when y+z>1
(NO) = nitrosyl where
  F = 0 to 5 when y+z=1 or F=1 to n when y+z>1
$C_p$ = cyclopentadienyl where
  G = 0 to 3 when w=z=1 or G=1 to n when y+z>1
$P_y$ = pyridine where
  H = 0 to 5 when y+z=1 or H=1 to n when y+z>1
Acac = acetylacetonate where
  I = 0 to 3 when y+z=1 or I=1 to n when y+z>1
$(AsR_3)$ = arsines, where R=H, alkyl or aryl and J=0 to 5 when y+z=1 or J=1 to n when y+z>1 the arsine also may be of the chelating type or contain mixed donating atoms e.g.
  $R_2As:R_2As$
  $R_2N:R_2P$
$(NR_3)$ = amines, where R=H, alkyl, or aryl and K=0 to 5 when y+z=1 or K=1 to n when y+z>1 as with arsines, a chelating or mixed donor chelating ligand may be employed.
$(PR_3)$ = phosphines where R=H, alkyl, or aryl and L=0 to 5 when g+z=1 or L=1to n when y+z>1 as with arsines, and amines, a chelating ligand may be employed.
$(SnX_3^-)$ or $(GeX^-)$ = trihalostannyl or trihalogermyl where X=F, Cl, Br, I and M=0 to 5 when y+z=1 or M=1 to n when y+z>1
(Carb) = carboxylate where N=0 to 5 when y+z=1 or N=1 to n when y+z>1
P = the bridging moiety/ligand between the metal and the resin support and Q=1 to n.

The compositions of the invention find use as catalysts in many chemical processes. Illustrative examples are the use of compositions containing rhodium or ruthenium complexes in hydroformylation-carbonylation, hydrogenation, isomerization and Fischer-Tropsch reactions. Compositions containing cobalt complexes are useful in hydroformylation, carbonylation, hydrogenation and isomerization reactions. Compositions containing molybdenum complexes are used in disproportionation (metathesis) and isomerization reactions. Compositions containing palladium and platinum complexes are useful in hydroformylation, carbonylation, isomerization, hydrogenation and oligomerization/dimerization reactions. Compositions containing nickel complexes are useful in oligomerization/dimerization reactions. Compositions containing tungsten or rhenium complexes are useful in metathesis reactions. Other reactions that can utilize the compositions of the invention will be apparent to one skilled in the art.

The composition of this invention and preparation thereof is described by the following illustrative embodiments which are provided for illustration and are not construed as limiting the invention.

ILLUSTRATIVE EMBODIMENTS

The catalyst preparation procedures described below were carried out in nitrogen-filled dry boxes. The solvent benzene was purified by distillation over $CaH_2$, all other solvents were of reagent-grade and used as supplied. The metal complexes $[Rh(CO)_2Cl]_2$, $Rh(PPh_3)_3Cl$, $Rh(NO_3)_3$ in $H_2O$, $Co_2(CO)_8$, $Ru(PPh_3)_3Cl_2$, $Mo(NO)_2Cl_2$, $PtCl_2(PPh_3)_2$, $[PtCl_2(PBu_3)]_2$, $Pd(C_6H_5CN)_2Cl_2$, $PdCl_2(PPh_3)_2$, $[Pd(allyl)Cl]_2$ and $Pd(OAc)_2$, and compounds $CH_3Br$, $SnCl_2 \cdot 2H_2O$, isonicotinic acid, and phosphines $[(CH_3)N]_3P$, $[(CH_3)_2NC_6H_4]_3P$, $[(CH_3)_2NCH_2CH_2O]_3P$ were used as supplied. The quaternized aminophosphines were prepared by the reaction of 1 equivalent of $CH_3Br$ with an aminophosphine in toluene solution at room temperature. The quaternized aminophosphine precipitated readily from the toluene solution. The complex $Ru(CO)_3(PPh_3)_2$ (J. Chem. Soc Dalton, 399 (1976)), $PtH(SnCl_3)(PPh_3)_2$ and $PtH(SnCl_3)(CO)(PPh_3)_2$ (J. Am. Chem. Soc. 97, 3553 (1975)) were prepared as described in the references. The resins are indicated by (resin backbone)-(exchange group), e.g. a sulfonated styrene divinylbenzene resin would be (styrene-divinyl benzene)-$(SO_3^-)$, etc. Ph, $C_6H_5$ and $\phi$ are used as abbreviations for phenyl; —$\phi$— and $C_6H_4$ indicates p-substituted benzene moieties.

PREPARATION OF RESIN-LINKING COMPOUND MOIETY

EXAMPLE 1

Preparation of sulfonated styrene-divinylbenzene resin/$[(CH_3)_2N]_3P$ Compound The aminophosphine $[(CH_3)_2N]_3P$ (0.98 g, 60 mmol) was dissolved in 175 ml of acetone in a 250 ml round-bottomed flask. 5.0 Grams of Rohm and Haas XN1010H+ resin (acid form; macroreticular sulfonated styrene-divinylbenzene, 3.3 meq/g) which had previously been thoroughly washed with deionized water and dried was added to the flask. The mixture was then stirred magnetically from the side of the flask for 48 hours to prevent resin attrition. The resin was filtered by suction, washed with 3×50 ml of acetone, and dried in vacuum oven (50° C.) overnight. Analysis showed the product as having the approximate formula (styrene-divinylbenzene)-$(SO_3^-)_{1.5}$ $[([(CH_3)_2N]_3P)(H^+)_{1.5}]$.

EXAMPLE 2

Preparation of sulfonated styrene-difinylbenzene resin/$[(CH_3)_2N\ C_6H_4]_3P$ compound The aminophosphine $[(CH_3)_2NC_6H_4]_3P$ (14.0 g, 35.8 mmol) was dissolved in 1000 ml warm benzene, cooled to room tempertaure, and filtered into a 2-1 round-bottomed flask quickly. 10.0 G of XN1010H+ ion-exchange resin was added, and the mixture stirred magnetically on side of flask for 72 hours. The resin was then filtered, washed with benzene and vacuum dried in oven (40° C.). Analysis showed the product as having the approximate formula (styrene-divinylbenzene)-$(SO_3^-)_{1.5}([(CH_3)_2NC_6H_4]_3P)(H^+)_{1.5}$.

EXAMPLE 3

Preparation of sulfonated styrene-divinylbenzene resin/$[(CH_3)_2NCH_2CH_2O]_3P$ compound This material was prepared in a similar manner as in Example 1 except that 3.54 g (12.0 mmol) of the aminophosphine $[(CH_3)_2NCH_2CH_2O]_3P$, 10.0 g of XN1010H+ resin, and 300 ml of acetone were used. Analysis showed the product as having the approximate formula (styrene-divinylbenzene)-$(SO_3^-)_{1.5}$ $[([(CH_2)_2NCH_2CH_2O]_3P)(H^+)_{1.5}]$.

EXAMPLE 4

Preparation of sulfonated styrene-divinylbenzene resin $[(\phi_2PCH_2CH_2)_2NCH_2CH_3]$ compound This material was prepared in a similar manner to Example 1 except that 2.82 g (6 mmol) of the aminophosphine $(\phi_2PCH_2CH_2)_2NCH_2CH_3$ and 200 ml of acetone was used. Analysis showed the product as having the approximate formula (styrene-divinylbenzene)-$(SO_3^-)_{1.5}[([(C_6H_5)_2PCH_2CH_2]_2NCH_2CH_3)(H^+)_{1.5}]$.

EXAMPLE 5

Preparation of sulfonated styrene-divinylbenzene resin/methylquaternized $[(CH_3)_2N]_3P$ compound The quaternized aminophosphine $([(CH_3)_2N]_3P)(CH_3^+)Br^-$ (7.0 g wet) was dissolved in 350 ml of deionized water in a 500 ml round-bottom flask. 10.0 G of XN1010Na ion-exchange resin (prepared by exhaustive ion-exchange of XN1010H+ with 10 l of 1 N NaCl or when the pH of the effluent wash was neutral) was added. The mixture was side-stirred for 48 hours, filtered with suction, and the resin washed with 5×100 deionized $H_2O$, then vacuum dried in oven overnight (45° C.). Analysis showed the product as having the approximate formula (styrene-divinylbenzene)-$(SO_3^-)[([(CH_3)_2N]_3P)(CH_3^+)]$.

EXAMPLE 6

Preparation of sulfonated styrene-divinyl benzene resin/methylquaternized $([(CH_3)_2NC_6H_4]_3P)$ compound This material was prepared in a similar manner as in Example 5 except that 10.4 (21.1 mmol) of the quaternized aminophosphine, 12.0 g of XN1010Na, and 1900 ml of an acetone/$H_2O$(12:7 v/v) solution were used. Analysis showed the product as having the approximate formula (styrene-divinylbenzene)-$(SO_3^-)[([(CH_3)_2NC_6H_4]_3P)(CH_3^+)]$.

EXAMPLE 7

Preparation of sulfonated styrene-divinylbenzene resin/methylquaternized $[(CH_3)_2NCH_2CH_2O]_3P$ compound This material was prepared in a similar manner as in Example 5 except that 5.6 g (14.4 mmol) of the quaternized aminophosphine, 8.0 g of XN1010Na, and 400 ml of $H_2O$ were used. Analysis showed the product as having the approximate formula (styrene-divinylbenzene)-$(SO_3^-)[([(CH_3)_2NCH_2CH_2O]_3P)(CH_3^+)]$.

EXAMPLE 8

Preparation of sulfonated styrene-divinylbenzene resin/methylquaternized $([(C_6H_5)_2PCH_2CH_2]_2NCH_2CH_3)$ compound This material was prepared in a similar manner as in Example 5 except that 2.0 g (3.5 mmol) of the quaternized aminophosphine, 4.0 g of XN1010Na, and 200 ml of deionized water were used. Analysis showed the product as having the approximate formula (styrene-divinylbenzene)-$(SO_3^-)$ $[([(C_6H_5)_2PCH_2CH_2]_2NCH_2CH_3)(CH_3^+)]$.

EXAMPLE 9

Preparation of sulfonated styrene resin/$[(CH_3)_2NC_6H_4]_3P$ compound

This material was prepared in a manner similar to Example 2 except that Dow MSC-1H resin (sulfonated polystrene, macroreticular, 1.6 meq/g) was used. Analysis showed the product as having the approximate formula (styrene)-$(SO_3^-)_{1.5}[([(CH_3)_2NC_6H_4]_3P)(H^+)_{1.5}]$.

EXAMPLE 10

Preparation of sulfonated styrene resin/methylquaternized $([(CH_3)_2NC_6H_4]_3P)$ compound 50 Grams of the hydrogen form of BioRad AG 50w-X1 (sulfonated polystyrene, 5.0 meq/g) was placed in a coarse fritted glass funnel which was then Na exchanged with 1 liter of 1 N NaCl by adding the salt solution in aliquots so it slowly ran through the resin. The resin was then washed in a similar manner with 2 liters of deionized water. This was followed by an acetone rinse and the resin was dried in a vacuum oven at about 40° C. for 2 days. A 5.0 g portion of the dried Na form of the resin was then added to 2 liters of an acetone-water solution (1:1 v/v) which contained the quaternized aminophosphine (2.0 g, 4.1 mmol) and stirred overnight under $N_2$. The material was then filtered and washed with an acetone solution, a water solution and then air-dried. Analysis showed the product as having the approximate formula (styrene)-$(SO_3^-)[([(CH_3)_2NC_6H_4]_3P)(CH_3^+)]$.

EXAMPLE 11

Preparation of phosphonated styrene-divinylbenzene resin/methylquaternized $([(CH_3)_2NC_6H_4]_3P)$ compound This material was prepared in a manner similar to Example 10 except that 5.0 g of Bio-Rex 63 (microreticular(gel), phosphonated, 6.6 meq/g) was used. Analysis showed the product as having the approximate formula (styrene-divinylbenzene)-$(PO_3^-)[([(CH_3)_2NC_6H_4]_3P)(CH_3^+)]$.

EXAMPLE 12

Preparation of carboxylated acrylic resin/methylquaternized $([(CH_3)_2NC_6H_4]_3P)$ This material was prepared in a manner similar to Example 10 except that 5.0 g of Bio-Rex 70 (acrylic polymer, carboxylic acid exchange group, 10.2 meq/g) was used. Analysis showed the product as having the approximate formula acrylic $(CO_2^-)[([(CH_3)_2NC_6H_4]_3P)(CH_3^+)]$.

EXAMPLE 13

Preparation of vinyl pyridinium resin/[o-$^-$O$_2$CC$_6$H$_5$P(C$_6$H$_5$)$_2$] compound A 10 g portion of Bio-Rex 9 (100–200 mesh, polymerized vinylpyridine, pyridinium type, 3.7 meq/g) was placed in a coarse grade fritted glass funnel and treated with 1 liter of 0.1 N HCl in the manner described in Example 10. The resin was then rinsed with 2 liters of deionized water, and finally with acetone. The resin was then dried for 2 days at about 40° C. in a vacuum oven.

A 5.0 g portion of resin was then added to about 500 ml of H$_2$O in a round bottom flask. A 1.29 g (3.8 mmol) of diphenyl(2-carboxyphenyl)phosphine was placed in a small flask of H$_2$O/acetone (5.0 g H$_2$O, 5.0 ml acetone) with 0.15 g of dissolved NaOH. After the phosphine was dissolved the solution of phosphine was added to the solution which contained the resin. This was stirred overnight under an N$_2$ atmosphere. The material was filtered and washed with a 50—50 v/v mix of acetone/water and finally with acetone. Analysis showed the product having the approximate formula (ethylene)-(pyridinium$^+$) [o-O$_2$CC$_6$H$_5$P(C$_6$H$_5$)$_2^-$]

EXAMPLE 14

Preparation of quaternary ammonium styrene-divinylbenzene resin/(HO$_2$CC$_5$H$_4$ N) compound To a solution of sodium hydroxide (1.5 g) in 150 ml of deionized H$_2$O was added 4.6 g (38.4 mmol) of isonicotinic acid. To the resultant solution was added 6.0 g of Bio-Rad AG-1 (styrene-divinyl benzene microreticular anion-exchange resin, Cl-form, 20–50 mesh, 3.2 meq/g), side-stirred for 2 hours, and filtered by suction. The resin material was then washed with 3×50 ml of acetone, and dried in vacuum oven (45° C.). Analysis showed a product having the approximate formula (styrene-divinylbenzene)-[CH$_2$N$^+$(CH$_3$)$_3$]($^-$O$_2$CC$_5$H$_4$N).

EXAMPLE 15

Preparation of quaternary ammonium styrene resin/(HO$_2$CC$_5$H$_4$N)

This material was prepared in a similar manner as in Example 14 except that 5.9 g (48.0 mmol) of isonicotinic acid and 6.0 g of the Dow MSA-1 (macroreticular polystyrene base-quaternary exchange group, 4.0 meq/g) resin were used. Analysis showed a product having the approximate formula (styrene)-[CH$_2$N$^+$(CH$_3$)$_3$]($^-$O$_2$CC$_5$H$_4$N).

PREPARATION OF RESIN-LINKING COMPOUND-METAL COMPLEX COMPOSITIONS

EXAMPLE 16

Preparation of sulfonated styrene-divinylbenzene resin/[(CH$_3$)$_2$N]$_3$P/rhodium complex composition The rhodium dimer [Rh(CO)$_2$Cl]$_2$ (0.66 g, 1.7 mmol) was dissolved in 85 ml of benzene in a 100 ml round-bottomed flask, 1.5 g of the resin material prepared as described in Example 1 was added. The mixture was side-stirred magnetically for 1.5 hours, filtered by suction, and the resin washed with 3×50 ml of benzene. The resultant composition was dried under vacuum in an oven (45° C.) to give a material analyzed by neutron activation to have 8.4%w Rh and 2.9%w P. Analysis showed a composition having the approximate formula (styrene-divinylbenzene)-(SO$_3^-$)$_{1.5}$[([(CH$_3$)$_2$N]$_3$P)(H$^+$)$_{1.5}$][Rh(CO)$_2$Cl]$_{0.9}$.

EXAMPLE 17

Preparation of sulfonated styrene-divinylbenzene resin/[(CH$_3$)$_2$NC$_6$H$_4$]$_3$P/rhodium complex composition A 2.0 g sample of the aminophosphine resin material prepared in example 2 was added to ca 25 mls of dry benzene in a 500-ml flash. To this mixture was added 0.12 gms (0.31 mmol) of (Rh(CO)$_2$Cl)$_2$. The entire reaction sequence was performed in a helium filled dry box.

The mixture was stirred for a 1.5 hour period and filtered to collect the composition which was washed with dry benzene and allowed to dry. The composition was stored in a tightly capped bottle in the dry box prior to use. Analysis showed a composition having the approximate formula (styrene-divinylbenzene)-(SO$_3^-$)$_{1.5}$[([(CH$_3$)$_2$NC$_6$H$_4$]$_3$)(H$^+$)$_{1.5}$][Rh(CO)$_2$Cl]$_{0.4}$.

EXAMPLE 18

Preparation of sulfonated styrene-divinylbenzene resin/[(CH$_3$)$_2$NC$_6$H$_4$]$_3$P/Rhodium complex composition A 0.3 g sample of the aminophosphine/resin material prepared in Example 2 was treated in a similar manner as described in Example 17 except that 0.28 g (0.3 mmol) of Rh ($\phi_3$P)$_3$Cl was used as the metal source. Analysis showed the composition having the approximate formula (styrene-divinylbenzene)-(SO$_3^-$)[([(CH$_3$)$_2$NC$_6$H$_4$]$_3$P)$_x$(H$^+$)$_{1.5}$](RhCl[$\phi_3$P]$_{3-x}$)$_{0.04}$ where x×1-3 because the aminophosphine can replace 1, 2 or 3 of the triphenyl phosphine ligands on the metal complex.

EXAMPLE 19

Preparation of sulfonated styrene-divinylbenzene resin/[(CH$_3$)$_2$NCH$_2$CH$_2$O]$_3$P/rhodium-complex composition This material was prepared in a similar manner as in Example 16 except that 0.61 g (1.6 mmol) of rhodium dimer (Rh(CO)$_2$Cl)$_2$ and the aminophosphine/resin material prepared as described in Example 3 were used. Analysis showed the composition having the approximate formula (styrene-divinylbenzene)-(SO$_3^-$)$_{1.5}$[([(CH$_3$)$_2$NCH$_2$CH$_2$O]$_3$P)(H$^+$)$_{1.5}$][Rh(CO)$_2$Cl]$_{0.8}$

EXAMPLE 20

Preparation of sulfonated styrene-divinylbenzene resin/[($\phi_2$PCH$_2$CH$_2$)$_2$NCH$_2$CH$_3$]/rhodium-complex composition This material was prepared in a similar manner as in Example 16 except that 0.48 g (1.23 mmol) of [Rh(CO)$_2$Cl]$_2$ and the aminophosphine resin material prepared as described in Example 4 were used. Analysis showed the composition as having the approximate formula (styrene-divinyl-benzene)-(SO$_3^-$)$_{1.5}$[([(C$_6$H$_5$)$_2$PCH$_2$CH$_2$]$_2$NCH$_2$CH$_3$)(H$^+$)$_{1.5}$][Rh(CO)$_2$Cl]$_{0.3}$.

EXAMPLE 21

Preparation of sulfonated styrene-divinylbenzene resin/methylquaternized [(CH$_3$)$_2$N]$_3$P/rhodium complex composition This material was prepared in a similar manner as in Example 16 except that 0.68 g (1.7 mmol) of [Rh(CO)$_2$Cl]$_2$ and 3.0 g of the aminophosphine resin material prepared as described in Example 5 were used. Analysis showed the composition as having the approximate formula (styrene-divinylbenzene)-(SO$_3$⁻)[([(CH$_3$)$_2$N]$_3$P)(CH$_3$⁺)][Rh(CO)$_2$Cl]$_{1.4}$.

EXAMPLE 22

Preparation of sulfonated styrene-divinylbenzene resin/methylquaternized ([(CH$_3$)$_2$NC$_6$H$_4$]$_3$P)/rhodium-complex composition The aminophosphine/resin material prepared in Example 6 (2.0 gm) was treated with 0.17 gm (0.43 mmol) of [Rh(CO)$_2$Cl]$_2$ in benzene solution in a helium filled dry box in a manner similar to that described in Example 17. Analysis showed the composition as having the approximate formula (styrene-divinylbenzene)-(SO$_3$⁻)[([(CH$_3$)$_2$NC$_6$H$_4$]$_3$P)(CH$_3$⁺)][Rh(CO)$_2$Cl]$_{0.5}$.

EXAMPLE 23

Preparation of styrene-divinylbenzene resin/methylquaternized [(CH$_3$)$_2$NCH$_2$CH$_2$O]$_3$P/rhodium complex composition This material was prepared in a similar manner as in Example 16 except that 0.08 g (0.21 mmol) of [Rh(CO)$_2$Cl]$_2$ and the aminophosphine resin material prepared as described in Example 7 were used. Analysis showed the composition as having the approximate formula (styrene-divinylbenzene)-(SO$_3$⁻)[([(CH$_3$)$_2$NCH$_2$CH$_2$O]$_3$P)(CH$_3$⁺)][Rh(CO)$_2$Cl]$_6$.

EXAMPLE 24

Preparation of sulfonated styrene-divinylbenzene resin/methylquaternized ([(C$_6$H$_5$)$_2$PCH$_2$CH$_2$]$_2$NCH$_2$CH$_3$)/rhodium-complex compound This material was prepared in a similar manner as in Example 16 except that 0.45 g (1.2 mmol) of the [Rh(CO)$_2$Cl]$_2$ rhodium and 1.2 g of the aminophosphine/resin material prepared as described in Example 8 were used. Analysis showed a composition having the approximate formula (styrene-divinylbenzene)-(SO$_3$⁻)[([(C$_6$H$_5$)$_2$PCH$_2$CH$_2$]$_2$NCH$_2$CH$_3$)(CH$_3$⁺)][Rh(CO)$_2$Cl]$_{0.5}$.

EXAMPLE 25

Preparation of sulfonated styrene resin/methylquaternized ([(CH$_3$)$_2$NC$_6$H$_4$]$_3$P)/rhodium-complex composition This material was prepared in a manner similar to example 19 except that 0.26 g (0.68 mmol) of [Rh(CO)$_2$Cl]$_2$ and 1.2 g of the aminophosphine/resin material prepared as described in Example 10 were used. Analysis showed the composition as having the approximate formula (styrene)-(SO$_3$⁻)[([(CH$_3$)$_2$NC$_6$H$_4$]$_3$P)(CH$_3$⁺][Rh(CO)$_2$Cl]$_{0.01}$.

EXAMPLE 26

Preparation of phosphonated styrene-divinylbenzene resin/methylquaternized ([(CH$_3$)$_2$NC$_6$H$_4$]$_3$P)/rhodium-complex composition In the manner described in Example 17, a 4.5-gm sample of the aminophosphine/resin material prepared in example 11 was treated with 0.26 gms (0.68 mmol) of [Rh(CO)$_2$Cl]$_2$. Analysis showed a composition having the approximate formula (styrene-divinylbenzene)-(PO$_3$⁻) [([(CH$_3$)$_2$NC$_6$H$_4$]$_3$P) (CH$_3$⁺)][Rh(CO)$_2$Cl]$_{0.1}$.

EXAMPLE 27

Preparation of carboxylated acrylic resin/methylquaternized ([(CH$_3$)$_2$NC$_6$H$_4$]$_3$P)/rhodium-complex composition In the manner described in Example 17, a 4.5-gm sample of the aminophosphine/resin material prepared in example 12 was treated with 0.26 gms (0.68 mmol) of [Rh(CO)$_2$Cl]$_2$. Analysis showed the composition as having the approximate formula (acrylic)-(CO$_2$⁻)[([(CH$_3$)$_2$NC$_6$H$_4$]$_3$P)(CH$_3$⁺)][Rh(CO)$_2$Cl]$_{0.01}$.

EXAMPLE 28

Preparation of vinylpyridinium resin/[o-⁻O$_2$CC$_6$H$_5$P(C$_6$H$_5$)$_2$]/rhodium-complex composition In the manner described in Example 17, a 2.4 gm sample of the phosphinobenzoic acid/resin material prepared in Example 13 was treated with 0.14 gms (0.34 mmol) of [Rh(CO)$_2$Cl]$_2$. Analysis showed the composition having the approximate formula (ethylene)-(pyridinium⁺) [o-⁻O$_2$CC$_6$H$_5$P(C$_6$h$_5$)$_2$][Rh(CO)$_2$Cl]$_{0.05}$.

EXAMPLE 29

Preparation of sulfonated styrene-divinylbenzene resin/methylquaternized ([(CH$_3$)$_2$NC$_6$H$_4$]$_3$P)/rhodium-complex composition In the manner described in Example 17, a 0.5-gm sample of the aminophosphine/resin material prepared in example 6 was treated with 0.44 gm (0.48 mmol) Rh($\phi_3$Cl). Analysis showed the composition as having the approximate formula (styrene-divinylbenzene)-(SO$_3$⁻)$_x$ [([(CH$_3$)$_2$N C$_6$H$_4$]$_3$P)(CH$_3$⁺)]$_x$ (RhCl[P(C$_6$H$_5$)$_3$]$_3$)$_{3-x}$)$_{0.05}$ where x=1, 2 or 3.

EXAMPLE 30

Preparation of sulfonate styrene-divinylbenzene resin/[(CH$_3$)$_2$N]$_3$P/cobalt-complex composition This material was prepared in a similar manner as in Example 16 except that the cobalt dimer Co$_2$(CO)$_8$ (0.58 g, 1.7 mmol) was used instead of the rhodium dimer. Analysis showed the composition as having the approximate formula (styrene-divinylbenzene)-(SO$_3$⁻)$_{1.5}$[([(CH$_3$)N]$_3$P)(H⁺)$_{1.5}$][Co(CO)$_4$]$_{0.5}$.

EXAMPLE 31

Preparation of sulfonated styrene-divinylbenzene resin/[(CH$_3$)$_2$NC$_6$H$_4$]$_3$P/cobalt-complex composition This material was prepared in a similar manner as in Example 17 except that the complex dicobalt octacarbonyl (0.5 g, 1.45 mmol) and 2.0 g of the aminophosphine/resin material prepared as described in Example 2 were used. Analysis showed the compositions as having the approximate formula (styrene-divinylbenzene)-$(SO_3^-)_{1.5}[([(CH_3)_2NC_6H_4]_3P)(H^+)_{1.5}][Co(CO)_4]_{0.8}$.

EXAMPLE 32

Preparation of sulfonated styrene-divinylbenzene resin/$[(CH_3)_2NCH_2CH_2O]_3P$/cobalt-complex composition This material was prepared in a similar manner as in Example 19 except that the complex $Co_2(CO)_8$ (0.54 g, 1.6 mmol) was used. Analysis showed the composition as having the approximate formula (styrene-divinylbenzene)-$(SO_3^-)_{1.5}[([(CH_3)_2NCH_2CH_2O]_3P)(H^+)_{1.5}][Co(CO)_4]_{0.3}$.

EXAMPLE 33

Preparation of sulfonated styrene-divinylbenzene resin/$[(\phi_2PCH_2CH_2)_2NCH_2CH_3]$/cobalt-complex composition This material was prepared in a similar manner as in Example 20 except that the complex $Co_2(CO)_8$ (0.42 g, 1.3 mmol) was used. Analysis showed the compositions as having the approximate formula (styrene-divinylbenzene)-$(SO_3^-)_{1.5}[([(C_6H_5)_2PCH_2CH_2]_2NCH_2CH_3)(H^+)_{1.5}]$-$[Co(CO)_4]_{0.2}$.

EXAMPLE 34

Preparation of sulfonated styrene-divinylbenzene resin/methylquaternized $[(CH_3)_2N]_3P$/cobalt-complex This material was prepared in a similar manner as in Example 21 except that the complex $Co_2(CO)_8$ (0.6 g, 1.7 mmol) and 24 g of the aminophosphine/resin material prepared as described in Example 5 were used. Analysis showed the composition as having the approximate formula (styrene-divinylbenzene)-$(SO_3^-)[([(CH_3)_2N]_3P)(CH_3^+)][Co(CO)_4]_{0.8}$.

EXAMPLE 35

Preparation of sulfonated styrene-divinylbenzene resin/methylquaternized $([(CH_3)_2NC_6H_4]_3P)$/cobalt-complex composition This material was prepared in a similar manner as in Example 22 except that the complex $Co_2(CO)_8$ (0.14 g, 0.4 mmol) and 20 g of the aminophosphine resin material prepared as described in Example 6 were used. Analysis showed the composition as having the approximate formula (styrene-divinylbenzene)-$(SO_3^-)[([(CH_3)_2NC_6H_4]_3P)(CH_3^+)][Co(CO)_4]_{1.8}$.

EXAMPLE 36

Preparation of sulfonated styrene-divinylbenzene resin/methylquaternized $[(CH_3)_2NCH_2CH_2O]_3P$/cobalt-complex composition This material was prepared in a similar manner as in Example 23 except that the complex $Co_2(CO)_8$ (0.07 g, 0.2 mmol) was used. Analysis showed the composition as having the approximate formula (styrene-divinylbenzene)-$(SO_3^-)$ $[([(CH_3)_2NCH_2CH_2O]_3P)(CH_3^+)][Co(CO)_4]_2$.

EXAMPLE 37

Preparation of sulfonated styrene-divinylbenzene resin/methylquaternized $([(C_6H_5)_2PCH_2CH_2]_2NCH_2CH_3)$/cobalt-complex composition This material was prepared in a similar manner as in Example 24 except that the complex $Co_2(CO)_8$ (0.4 g, 1.2 mmol) was used. Analysis showed the composition of having the approximate formula (styrene-divinylbenzene)-$(SO_3^-)$ $[([(C_6H_5)_2PCH_2CH_2]_2NCH_2CH_3)(CH_3^+)][Co(CO)_4]_{0.3}$.

EXAMPLE 38

Preparation of sulfonated styrene-divinylbenzene resin/$[(CH_3)_2NC_6H_4]_3P$/ruthenium-complex composition This material was prepared in a similar manner as in Example 17 except that the ruthenium complex $Ru(\phi_3P)_3Cl_2$ (1.0 g, 1.1 mmol) and 1.0 g of aminophosphine/resin material prepared as described in Example 2 were used. Analysis showed the composition as having the approximate formula (styrene-divinylbenzene)-$(SO_3^-)_{1.5x}$ $[([(CH_3)_2NC_6H_4]_3P)_x(H^+)_{1.5x}](RuCl_2[P(C_6H_5)_3]_{3-x})_{0.2}$ where x=1, 2, or 3.

EXAMPLE 39

Preparation of sulfonated styrene-divinylbenzene resin/methylquaternized $([(CH_3)_2NC_6H_4]_3P)$/ruthenium complex composition This material was prepared in a similar manner as in Example 22 except the ruthenium complex $Ru(\phi_3P_3)_3Cl_2$(0.19 g, 0.2 mmol) and 1.0 g of aminophosphine/resin material prepared as described in Example 6 were used. Analysis showed the composition as having the approximate formula (styrene-divinylbenzene)-$(SO_3^-)_x[([(CH_3)_2NC_6H_4]_3P)(CH_3^+)]_x$ $(RuCl_2[P(C_6H_5)_3]_{3-x})_{0.05}$ where x=1, 2, or 3.

EXAMPLE 40

Preparation of sulfonated styrene-divinylbenzene resin/$[(CH_3)_2N]_3P$/ruthenium complex composition This material was prepared in a similar manner as in Example 16 except that the ruthenium complex $Ru(CO)_3(\phi_3P)_2$ (1.1 g, 1.6 mmol) was used. Analysis showed the composition as having the approximate formula (styrene-divinylbenzene)-$(SO_3^-)_{1.5x}[([(CH_3)_2N]_3P)_x(H^+)_{1.5x}][Ru(CO)_3[P(C_6H_5)_3]_{2-x})_{0.05}$ where x=1 or 2.

EXAMPLE 41

Preparation of sulfonated styrene-divinylbenzene methyl-quaternized $([(CH_3)_2NC_6H_4]_3P)$/ruthenium-complex composition This material was prepared in a similar manner as in Example 39 except the ruthenium complex $Ru(CO)_3(\phi_3P)_2$ (0.77 g, 1.1 mmol) was used. Analysis showed the composition as having the approximate formula (styrene-divinylbenzene)-$(SO_3^-)_x[([(CH_3)_2NC_6H_4]_3P)$-$(CH_3^+)]_x(Ru(CO)_3[P(C_6H_5)_3]_{2-x})_{0.04}$ where x=1 or 2.

EXAMPLE 42

Preparation of sulfonated styrene-divinylbenzene resin/[(CH$_3$)$_2$NCH$_2$CH$_2$O]$_3$P/ruthenium-complex composition This material was prepared in a similar manner as in Example 19 except that the ruthenium complex Ru(CO)$_3$($\phi_3$P)$_2$ (0.15 g, 0.21 mmol) was used. Analysis showed the composition as having the approximate formula (styrene-divinylbenzene)-(SO$_3^-$)1.5x[([(CH$_3$)$_2$NCH$_2$CH$_2$O]$_3$P)$_x$(H$^+$)1.5x](Ru(CO)$_3$[P(C$_6$H$_5$)$_3$]$_{2-x}$)$_{0.04}$ where x=1 or 2.

EXAMPLE 43

Preparation of sulfonated styrene-divinylbenzene resin/[($\phi_2$PCH$_2$)$_2$NCH$_2$CH$_3$]/ruthenium-complex composition This material was prepared in a similar manner as in Example 20 except that the ruthenium complex Ru(CO)$_3$($\phi_3$P)$_2$ (0.87 g, 1.2 mmol) was used. Analysis showed the composition as having the approximate formula (styrene-divinylbenzene)-(SO$_3^-$)$_x$[([(C$_6$H$_5$)$_2$PCH$_2$CH$_2$]$_2$NCH$_2$CH$_3$)(H$^+$)]$_x$(Ru(CO)$_3$[P(C$_6$H$_5$)$_3$]$_{2-x}$)$_{0.04}$ where x=1 or 2.

EXAMPLE 44

Preparation of sulfonated styrene-divinylbenzene resin/methyl-quaternized [(CH$_3$)$_2$N]$_3$P/ruthenium-complex composition This material was prepared in a similar manner in Example 21 except that the ruthenium complex Ru(CO)$_3$($\phi_3$P)$_2$ (1.23 g, 1.7 mmol) was used. Analysis showed the composition as having the approximate formula (styrene-divinylbenzene)-(SO$_3^-$)$_x$[([(CH$_3$)$_2$N]$_3$P)(CH$_3^+$)]$_x$(Ru(CO)$_3$[P(C$_6$H$_5$)$_3$]$_{2-x}$)$_{0.04}$ where x=1 or 2.

EXAMPLE 45

Preparation of sulfonated styrene-divinylbenzene resin/methyl-quaternized [(CH$_3$)$_2$NC$_6$H$_4$]$_3$P)/ruthenium-complex composition This material was prepared in a similar manner as in Example 22 except that the ruthenium complex Ru(CO)$_3$(P$\phi_3$)$_2$ (0.14 g, 0.2 mmol) and 1.0 g of the aminophosphine resin material prepared as described in Example 6 were used. Analysis showed the composition as having the approximate formula (styrene-divinylbenzene)-(SO$_3^-$)$_x$[([(CH$_3$)$_2$NC$_6$H$_4$]$_3$P)(CH$_3^+$)]$_x$ (Ru(CO)$_3$[P(C$_6$H$_5$)$_3$]$_{3-x}$)$_{0.01}$ where x=1 or 2.

EXAMPLE 46

Preparation of sulfonated styrene-divinylbenzene resin/methyl-quaternized [(CH$_3$)$_2$NCH$_2$CH$_2$O]$_3$P/ruthenium-complex composition This material was prepared in a similar manner as in Example 23 except that the ruthenium complex Ru(CO)$_3$($\phi_3$P)$_2$ (0.15 g, 0.2 mmol) was used. Analysis showed the composition as having the approximate formula (styrene-divinylbenzene)-(SO$_3^-$)[([(CH$_3$)$_2$NCH$_2$CH$_2$O]$_3$P)(CH$_3^+$)]$_x$(Ru(CO)$_3$[P(C$_6$H$_5$)$_3$]$_{2-x}$)$_{0.01}$ where x=1 or 2.

EXAMPLE 47

Preparation of sulfonated styrene-divinylbenzene resin/methyl-quaternized ([(C$_6$H$_5$)$_2$PCH$_2$CH$_2$]$_2$NCH$_2$CH$_3$)/ruthenium-complex composition This material was prepared in a similar manner as in Example 24 except that the ruthenium complex Ru(CO)$_3$($\phi_3$P)$_2$ (0.82 g., 1.2 mmol) was used. Analysis showed the composition as having the approximate formula (styrene-divinylbenzene)-(SO$_3^-$)$_x$[([(C$_6$H$_5$)$_2$PCH$_2$CH$_2$]$_2$NCH$_2$CH$_3$)(CH$_3^+$)]$_x$(Ru(CO)$_3$[P(C$_6$H$_5$)$_3$]$_{2-x}$)$_{0.01}$ where x=1 or 2.

EXAMPLE 48

Preparation of sulfonated styrene-divinylbenzene resin/methyl-quaternized ([CH$_3$)$_2$NC$_6$H$_4$]$_3$P)/molybdenum-complex composition To a 1-liter flask was added 1.73 g Mo(NO)$_2$Cl$_2$, 50 ml of methanol, and 15 g of aminophosphine/resin material prepared as described in Example 6. The mixture was stirred for 24 hours, the solid filtered and washed with methanol and dried under vacuum. Analysis showed the composition as having the approximate formula (styrene-divinylbenzene)-(SO$_3^-$)$_x$[([(CH$_3$)$_2$NC$_6$H$_4$]$_3$P)(CH$_3^+$)]$_x$ [Mo(NO)$_{2-x}$Cl$_{0.4}$]$_{0.3}$ where x=1 or 2.

EXAMPLE 49

Preparation of sulfonated styrene-divinylbenzene resin/[(CH$_3$)$_2$NC$_6$H$_4$]$_3$P/palladium-complex composition The aminophosphine/resin material (0.3 g) prepared in Example 2 was treated with 0.12 g (0.3 mmol) of Pd($\phi$CN)$_2$Cl$_2$ in a manner similar to that described in Example 17. Analysis showed the composition having the approximate formula (styrene-divinylbenzene)-(SO$_3^-$)$_{1.5x}$ [([(CH$_3$)$_2$NC$_6$H$_4$]$_3$P)$_x$(H$^+$)$_{1.5x}$][Pd(C$_6$H$_5$CN)$_{2-x}$Cl$_2$]$_{0.5}$ where x=1 or 2.

EXAMPLE 50

Preparation of sulfonated styrene-divinylbenzene resin/methyl-quaternized [(CH$_3$)$_2$NC$_6$H$_4$]$_3$P)/palladium-complex composition The aminophosphine/resin material (0.5 g) prepared in Example 6 was treated with 0.18 g (0.48 mmol) of Pd($\phi$CN)$_2$Cl$_2$ in a manner similar to that described in Example 17. Analysis showed the composition as having the approximate formula (styrene-divinylbenzene)-(SO$_3^-$)$_x$ [([(CH$_3$)$_2$NC$_6$H$_4$]$_3$P)(CH$_3^+$)]$_x$[Pd(C$_6$H$_5$CN)$_{2-x}$Cl$_2$]$_{0.5}$ where x=1 or 2.

EXAMPLE 51

Preparation of sulfonated styrene-divinylbenzene resin/[(CH$_3$)$_2$NC$_6$H$_4$]$_3$P/palladium-complex composition To a solution of 0.73 g (1.0 mmol) of PdCl$_2$($\phi_3$P)$_2$ in 70.0 ml CHCl$_3$ was added 2.0 g of the aminophosphine/resin material prepared as described in Example 2. The mixture was stirred for 1 hour, filtered, washed with CHCl$_3$, and dried under vacuum. The resultant composition was Soxhlet-extracted with methyl ethyl ketone for 4 hours, and dried in vacuum oven at approx. 40° C. Analysis showed the composition as having the approximate formula (styrene-divinylbenzene)-$(SO_3^-)_{1.5x}[([(CH_3)_2NC_6H_4]_3P)_x(H^+)_{1.5x}]$ $[PdCl_2[P(C_6H_5)_3]_{2-x}]_{0.2}$ where $x=1$ or 2.

EXAMPLE 52

Preparation of sulfonated styrene-divinylbenzene resin/$[(CH_3)_2NC_6H_4]_3P$/palladium-tin-complex composition 2.0 Grams of aminophosphine/resin material prepared as described in Example 51 (prior to the Soxhlet-extraction step) was added to a filtered solution of 1.2 g (5.2 mmol) of $SnCl_2 \cdot 2H_2O$ in 200 ml of acetone. The mixture was stirred on side for 1 hour, filtered, washed with acetone, vacuum dried, Soxhlet-extracted with methyl ethyl ketone for 4 hours, and dried in vacuum at 40° C. Analysis showed the composition as having the approximate formula (styrene-divinylbenzene)-$(SO_3^-)_{1.5x}[([(CH_3)_2NC_6H_4]_3P)_x(H^+)_{1.5x}](SnCl_2)_{0.2x}(PdCl_2[P(C_6H_5)_3]_{2-x})_{0.2}$ where $x=1$ or 2.

EXAMPLE 53

Preparation of sulfonated styrene divinylbenzene resin/$[(CH_3)_2NC_6H_4]_3P$/palladium-complex composition The palladium dimer $[Pd(allyl)Cl]_2$ (1.36 g, 3.5 mmol) was dissolved in 50 ml of toluene and stirred overnight with 5.0 g of aminophosphine/resin material prepared as described in Example 2. The resulting composition then filtered, washed with toluene, Soxhlet-extracted with toluene for 4 hours and dried under vacuum at 50° C. Analysis showed the composition as having the approximate formula (styrene-divinylbenzene)-$(SO_3^-)_{1.5x}[([(CH_3)_2NC_6H_4]P_3)_x(H^+)_{1.5x}][PdCl(C_3H_5)_{2-x}]_{0.2}$ where $x=1$ or 2.

EXAMPLE 54

Preparation of quaternary ammonium styrene-divinylbenzene resin/$HO_2CC_5H_4N$)/palladium-complex composition To a toluene solution of palladium acetate (1.0 g 4.4 mmol) was added 6 g of isonicotinic acid/resin material prepared as described in Example 14; the mixture stirred on the side overnight, filtered, and the resulting composition Soxhlet-extracted with toluene for 5 hours. The material was then dried in vacuum oven overnight (45° C.). Analysis showed the composition as having the approximate formula (styrene-divinylbenzene)-$[CH_2N^+(CH_3)_3]$ $(^-O_2CC_5H_4N)$ $[Pd(O_2CCH_3)_2]_{0.1}$.

EXAMPLE 55

Preparation of quaternary ammonium styrene-divinylbenzene resin/$(HO_2CC_5H_4N)$/palladium-complex composition This material was prepared in a similar manner as in Example 54 except the aminophosphine/resin material was that prepared as described in Example 15. Analysis showed the composition as having the approximate formula (styrene-divinylbenzene)-$[CH_2N^+(CH_3)_3]$ $(HO_2CC_5H_4N)$ $[Pd(O_2CCH_3)_2]_{0.1}$.

EXAMPLE 56

Preparation of sulfonated styrene-divinylbenzene resin/$[(CH_3)_2NC_6H_4]_3P$/platinum-tin-complex composition To an 90 ml acetone solution of the platinum complex $PtH(SnCl_3)(\phi_3P)_2$ (1.2 g 1.2 mmol) was added 2.0 g of the aminophosphine/resin material prepared as described in Example 2, side-stirred magnetically for 1.5 hours, filtered, the resultant composition washed with acetone, and vacuum dried at 45° C. Analysis showed the composition as having the approximate formula (styrene-divinylbenzene)-$(SO_3^-)_{1.5x}$ $[([(CH_3)_2NC_6H_4]_3P)(H^+)]_{1.5x}(PtH(SnCl_3)[P(C_6H_5)_3]_{2-x})_{0.1}$ where $x=1$ or 2.

EXAMPLE 57

Preparation of sulfonated styrene-divinylbenzene resin/methyl-quaternized $([(CH_3)_2NC_6H_4]_3P)$/platinum-tin-complex composition This material was prepared as in Example 56 except that 0.17 g (0.18 mmol) of the platinum complex and 1.0 g of the aminophosphine/resin material prepared as described in Example 6 were used. Analysis showed the composition as having the approximate formula (styrene-divinylbenzene)-$(SO_3^-)_x$ $[([(CH_3)_2NC_6H_4]_3P)(CH_3^+)]_x(PtH(SnCl_3)[P(C_6H_5)_3]_{2-x})_{0.04}$ where $x=1$ or 2.

EXAMPLE 58

Preparation of sulfonated styrene-divinylbenzene resin/methyl-quaternized $([(CH_3)_2NC_6H_4]_3P)$/platinum-tin-complex composition This material was prepared in a similar manner as in Example 56 except that the platinum complex $PtH(CO)(SnCl_3)(\phi_2P)_2$ was used instead and 200 ml of acetone was used. Analysis showed the composition as having the approximate formula (styrene-divinylbenzene)-$(SO_3^-)_{1.5x}$ $[([(CH_3)_2NC_6H_4]_3P)(CH_3^+)]_{1.5x}(PtH(SnCl_3)$ $[P(C_6H_5)_3]_{2-x})_{0.04}$ where $x=1$ or 2.

EXAMPLE 59

Preparation of sulfonated styrene-divinylbenzene resin/$[(CH_3)_2NC_6H_4]_3P$/platinum-tin-complex compositions To a 50 ml benzene solution of $[PtCl_2(Bu_3P)]_2$ (1.2 g, 1.2 mmol) was added 2.0 g of aminophosphine/resin material prepared as described in Example 2, the mixture stirred on the side magnetically for 1.5 hours, and filtered. The resultant filtrate was passed through the resin material on the filter by gravity three times, filtered, and then washed with benzene, and vacuum dried. The resin material was then added to a 400 ml acetone solution of $SnCl_2 \cdot 2H_2O$ (2.5 g), side-stirred for 40 min., filtered, washed with acetone, and vacuum-dried. Analysis showed the composition as having the formula (styrene-divinylbenzene)-$(SO_3^-)_{1.5}[([(CH_3)_2NC_6H_4]_3P)(H^+)_{1.5}](SnCl_2)_{0.2}[PtCl_2(n-C_4H_{10})_3P])_{0.2}$.

EXAMPLE 60

Preparation of sulfonated styrene-divinylbenzene resin/methyl-quaternized ([(CH$_3$)$_2$NC$_6$H$_4$]$_3$P)/platinum-tin-complex composition This material was prepared as described in Example 59 except that 0.33 g (0.36 mmol) of [PtCl$_2$(Bu$_3$P)]$_2$ was used and the aminophosphine/resin material was then prepared as described in Example 6. Analaysis showed the composition as having the formula (styrene-divinylbenzene)-(SO$_3^-$) [([(CH$_3$)$_2$NC$_6$H$_4$]$_3$P)(CH$_3^+$)](SnCl$_2$)$_{0.2}$(PtCl$_2$[(n-C$_4$H$_{10}$)$_3$P])$_{0.05}$.

PROCESSES UTILIZING COMPOSITIONS OF THE INVENTION

EXAMPLE 61

Hydroformylation Process

To a 300 ml ss Magnedrive autoclave was added 70 ml of benzene, 2.0 ml of n-decane (internal standard), 20.0 ml (160 mmol) of 1-hexene, and 0.5 g of the resin/ligand/cobalt catalyst as described in Example 31. The solution was deoxygenated with nitrogen. Synthesis gas (CO/H$_2$, 1:1, 1200 psig) was then charged to the reactor and the reactor is heated to 120° C. After 20 hours, gas chromatographic analysis revealed the following results:

| | |
|---|---|
| Conversion (mole%) | 47 |
| Selectivity to C$_7$-aldehyde (mole %) | 99 |
| Selectivity to hexane (mole %) | 1 |
| Linearity of C$_7$-aldehyde | 71 |
| Reaction Rate (mole/mole/hr) | 24 |

EXAMPLE 62

Hydrogenation process

To a 300 ml ss Magnedrive autoclave was added 80 ml of toluene, 2.0 ml of n-decane (internal standard), 10.0 ml (80 mmol) of 1-hexane, and 1.7 g of the resin/ligand/rhodium catalyst as described in Example 17. The solution was deoxygenated with nitrogen, and 500 psig of hydrogen was charged to the reactor. The reactor was then heated to 100° C. After 1 hour, gas chromatographic analysis revealed the following results:

| | |
|---|---|
| Conversion (mole %) | 67% |
| Selectivity to n-hexane (mole %) | 97% |
| Reaction Rate (mole/mole/hour) | 170 |

EXAMPLE 63

Olefin Metathesis (Disproportionation) Process

To a mixture of 4 ml of chlorobenzene, 2 ml of 1-hexene, 1.0 g of the resin/ligand/molybdenum composition prepared as described in Example 48 was added 200 ml of 25% Al$_2$(CH$_3$)$_3$Cl$_3$ in hexane. The mixture was stirred for 2 hours at room temperature. Analysis showed a 4.7% yield of decenes after 2 hours.

What is claimed is:

1. A composition comprising:
   (a) an ion exchange resin having a strongly acidic, weakly acidic, or mixed acid-base type functional group;
   (b) an element, selected from the transition group of elements; and
   (c) an organic linking compound of from 1 to about 100 carbon atoms which has at least one moiety selected from the group consisting of monohydrocarbyl ammonium, dihydrocarbyl ammonium, trihydrocarbyl ammonium, pyridinium and phosphonium which is ionically bonded to said ion exchange resin and further has at least one moiety which contains a heteroatom selected from the group consisting of trivalent nitrogen, trivalent phosphorus, trivalent arsenic, trivalent bismuth and trivalent antimony which is coordinately bonded to said element.

2. A composition comprising:
   (a) an ion exchange resin having a basic-type functional group;
   (b) an element selected from the transition group of elements; and
   (c) an organic linking compound of from 1 to about 100 carbon atoms which has at least one moiety derived from the group consisting of carboxylic acid, phosphonic acid, phosphinic acid, sulfenic acid, sulfinic acid, sulfonic acid, boronic acid and boronous acid which is ionically bonded to said ion exchange resin and further has at least one moiety which contains a heteroatom selected from the group consisting of trivalent nitrogen, trivalent phosphorus, trivalent arsenic, trivalent bismuth and trivalent antimony which is coordinately bonded to said element.

3. The composition of claim 1 wherein the functional group of the ion exchange resin is selected from the group consisting of sulfonic acid, fluorinated alkyl sulfuric acid, phosphonic acid, carboxylic acid and aminocarboxylic acid, the ionically bonded moiety is selected from the group consisting of monohydrocarbyl ammonium, dihydrocarbyl ammonium, trihydrocarbyl ammonium, quaternary ammonium, pydridinium and phosphonium, the coordinately bonded moiety contains a heteroatom selected from the group consisting of trivalent nitrogen and trivalent phsophorus and the metal is selected from Group VIB, VIIB, VII, and IB.

4. The composition of claim 3 wherein the ion exchange resin has a backbone selected from the group consisting of polymerized styrene, styrene-divinylbenzene, phenol-formaldehyde, benzene-formaldehyde, acrylic acid and methacrylic acid.

5. The composition of claim 2 wherein the functional group of the ion exchange resin is selected from the group consisting of primary, secondary, tertiary, quaternary amine and pyridinium, the ionically bonded moiety is selected from the group consisting of trivalent nitrogen and trivalent phosphorus and the metal is selected from Group VIB, VIIB, VIII and IB.

6. The composition of claim 5 wherein the ion exchange resin has a backbone selected from the group consisting of polymerized styrene, styrene-divinylbenzene, phenol-formaldehyde, benzene-formaldehyde, epoxypolyamine and phenolic-polyamine.

7. The composition of claim 1 wherein the element is selected from the group consisting of cobalt, ruthenium, molybdenum, tungsten, platinum, palladium and rhodium.

8. The composition of claim 3 wherein the element is selected from the group consisting of cobalt, ruthenium, molybdenum, tungsten, platinum, palladium and rhodium.

9. The composition of claim 2 wherein the element is selected from the group consisting of cobalt, ruthenium, molybdenum, tungsten, platinum, palladium and rhodium.

* * * * *